(12) United States Patent
Hoshiya et al.

(10) Patent No.: US 12,338,213 B2
(45) Date of Patent: Jun. 24, 2025

(54) METHOD FOR PRODUCING FLUOROALKOXIDE

(71) Applicant: DAIKIN INDUSTRIES, LTD., Osaka (JP)

(72) Inventors: Naoyuki Hoshiya, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/357,061

(22) Filed: Jun. 24, 2021

(65) Prior Publication Data

US 2021/0317061 A1 Oct. 14, 2021

Related U.S. Application Data

(63) Continuation of application No. PCT/JP2019/046774, filed on Nov. 29, 2019.

(30) Foreign Application Priority Data

Dec. 26, 2018 (JP) ................................. 2018-242558

(51) Int. Cl.
| | |
|---|---|
| C07C 51/04 | (2006.01) |
| C07C 29/64 | (2006.01) |
| C07C 41/01 | (2006.01) |
| C07C 51/41 | (2006.01) |
| C07C 67/28 | (2006.01) |
| C07C 67/29 | (2006.01) |
| C07C 209/68 | (2006.01) |

(52) U.S. Cl.
CPC .............. *C07C 51/04* (2013.01); *C07C 29/64* (2013.01); *C07C 41/01* (2013.01); *C07C 51/412* (2013.01); *C07C 67/28* (2013.01); *C07C 67/29* (2013.01); *C07C 209/68* (2013.01)

(58) Field of Classification Search
None
See application file for complete search history.

(56) References Cited

U.S. PATENT DOCUMENTS

| | | | |
|---|---|---|---|
| 3,449,389 A | 6/1969 | Warnell et al. | |
| 3,549,711 A * | 12/1970 | Madison | C07C 43/123 |
| | | | 558/450 |
| 4,628,094 A | 12/1986 | Farnham et al. | |
| 5,750,797 A * | 5/1998 | Vitcak | C07C 41/01 |
| | | | 568/681 |
| 6,023,002 A * | 2/2000 | Behr | C07C 43/12 |
| | | | 562/851 |
| 6,046,368 A * | 4/2000 | Lamanna | C07C 41/02 |
| | | | 568/681 |
| 6,403,832 B1 * | 6/2002 | Oikawa | C07C 217/58 |
| | | | 562/605 |
| 2004/0192974 A1 * | 9/2004 | Navarrini | C07C 41/01 |
| | | | 568/677 |
| 2007/0049776 A1 * | 3/2007 | Zhao | C07C 41/01 |
| | | | 568/683 |
| 2011/0251427 A1 * | 10/2011 | Murai | C08F 114/02 |
| | | | 562/605 |
| 2015/0045580 A1 * | 2/2015 | Hartwig | C07C 41/30 |
| | | | 568/629 |

(Continued)

FOREIGN PATENT DOCUMENTS

| | | |
|---|---|---|
| JP | 64-70427 A | 3/1989 |
| JP | 2-25439 A | 1/1990 |

(Continued)

OTHER PUBLICATIONS

Jelier ("A convenient Route to Tetraalkylammonium Perfluoroalkoxides from Hydrofluoroethers" Angew. Chem. Int. Ed. 2015, Supporting Information p. S1-S80). (Year: 2015).*

(Continued)

*Primary Examiner* — Amy C Bonaparte
(74) *Attorney, Agent, or Firm* — WENDEROTH, LIND & PONACK, L.L.P.

(57) ABSTRACT

An aim of the present disclosure is to provide a method for producing a fluoroalkoxide, said method being more useful than conventional methods, and the like. The aim can be achieved by a method for producing a compound represented by the following formula (1):

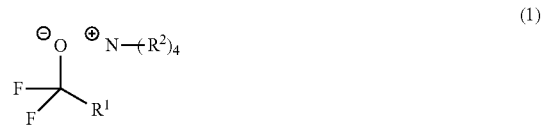

(1)

(wherein $R^1$ is a fluoroalkyl group optionally containing an oxygen atom between carbon atoms, or a fluoroalkoxy group optionally containing an oxygen atom between carbon atoms, and
each $R^2$ is identical to or different from each other and is a hydrocarbon group),
the method comprising the step of reacting
a compound represented by the following formula (2):

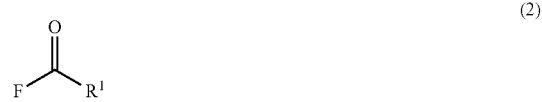

(2)

with a compound represented by the following formula (3):

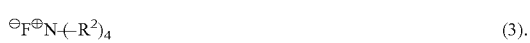

(3).

6 Claims, No Drawings

(56) References Cited

U.S. PATENT DOCUMENTS

2015/0336968 A1* 11/2015 Howell ............... C07D 487/18
508/304

FOREIGN PATENT DOCUMENTS

| JP | 2016-509597 A | 3/2016 |
|---|---|---|
| JP | 2018-77330 A | 5/2018 |
| WO | 2014/110329 | 7/2014 |
| WO | 2019/116262 | 6/2019 |
| WO | 2019/202079 | 10/2019 |

OTHER PUBLICATIONS

English language translation of JPS6470427, obtained Aug. 2022 (Year: 2022).*

Zhang et al., "The $OC_2F_5^-$, $OCF(Cf_3)_2^-$, and $OCFCF_2O^-$ Anions: Preparation and Structure", Inorganic Chemistry, 1997, vol. 36, pp. 5689-5693.

Jelier et al., "A Convenient Route to Tetraalkylammonium Perfluoroalkoxides from Hydrofluoroethers", Angewandte Chemie International Edition, 2015, vol. 54, pp. 2945-2949, Supporting Information (S1-S16).

Marrec et al., "A deeper insight into direct trifluoromethoxylation with trifluoromethyl triflate", Journal of Fluorine Chemistry, 2010, vol. 131, pp. 200-207.

Redwood et al., "Fully Fluorinated Alkoxides Part I. Trifluoromethoxides of Alkali Metals", Canadian Journal of Chemistry, 1965, vol. 43, No. 7, pp. 1893-1898.

International Search Report, dated Feb. 25, 2020, issuing in counterpart application No. PCT/JP2019/046774.

Extended European Search Report issued Sep. 8, 2022 in corresponding European Patent Application No. 19904504.8.

* cited by examiner

METHOD FOR PRODUCING FLUOROALKOXIDE

TECHNICAL FIELD

This disclosure relates to a method for producing a fluoroalkoxide.

BACKGROUND ART

Several methods are known as methods for producing fluoroalkoxide.

For example, Non-Patent Literature (NPL) 1 discloses reacting carbonyl fluoride with potassium fluoride to thereby obtain potassium perfluoromethoxide.

Patent Literature (PTL) 1 discloses reacting $CF_3CF_2CF_2OCH_3$ with trimethylamine to thereby obtain tetramethylammonium perfluoropropoxide.

Patent Literature (PTL 2) discloses reacting trifluoroacetylfluorolide with tris(dimethylamino)sulfonium difluorotrimethyl silicate to thereby obtain tris(dimethylamino) sulfonium perfluoroethoxide.

CITATION LIST

Patent Literature

PTL 1: JP2016-509597A
PTL 2: U.S. Pat. No. 4,628,094

Non-Patent Literature

NPL 1: Can. J. Chem. 1965, 43, 1893

SUMMARY

The present disclosure includes the following embodiments.

A method for producing a compound represented by the following formula (1):

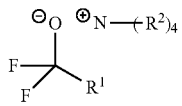

(1)

(wherein $R^1$ is a fluoroalkyl group optionally containing an oxygen atom between carbon atoms, or a fluoroalkoxy group optionally containing an oxygen atom between carbon atoms, and
each $R^2$ is identical to or different from each other and is a hydrocarbon group),
the method comprising the step of reacting
a compound represented by the following formula (2):

(2)

(wherein $R^1$ is as defined above)

with a compound represented by the following formula (3):

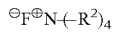

(3)

(wherein $R^2$ is as defined above).

The present disclosure also includes the following embodiments.

A composition comprising
a compound represented by formula (1):

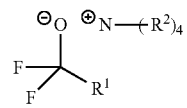

(1)

(wherein $R^1$ is a fluoroalkyl group optionally containing an oxygen atom between carbon atoms, or a fluoroalkoxy group optionally containing an oxygen atom between carbon atoms, and
each $R^2$ is identical to or different from each other and is a hydrocarbon group), and
a compound represented by formula (4):

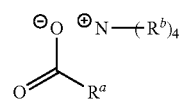

(4)

(wherein $R^a$ is a fluoroalkyl group optionally containing an oxygen atom between carbon atoms, or a fluoroalkoxy group optionally containing an oxygen atom between carbon atoms, and
each $R^b$ is identical to or different from each other and is a hydrocarbon group),
wherein when the sum of the content of the compound represented by formula (1) and the content of the compound represented by formula (4) is defined as 100%, the content of the compound represented by formula (1) is 70% or more in terms of molar ratio.

The present disclosure further includes the following embodiments.

A method for producing a compound represented by the following formula (5):

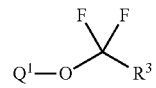

(5)

(wherein $R^3$ is a fluoroalkyl group optionally containing an oxygen atom between carbon atoms, or a fluoroalkoxy group optionally containing an oxygen atom between carbon atoms, and
$Q^1$ is an organic group),
the method comprising the step of reacting
a compound represented by the following formula (6):

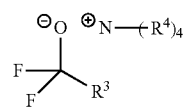

(6)

(wherein $R^3$ is as defined above, and each $R^4$ is identical to or different from each other and is a hydrocarbon group)

with a compound represented by the following formula (7):

$$Q^1\text{-L} \tag{7}$$

(wherein $Q^1$ is as defined above and L is a leaving group).

Advantageous Effects

According to the present disclosure, a method for producing a fluoroalkoxide, the method being more useful than conventional methods, and the like are provided.

DESCRIPTION OF EMBODIMENTS

The above summary of the present disclosure is not intended to describe each disclosed embodiment or every implementation of the present disclosure.

The description of the present disclosure that follows more specifically exemplifies illustrative embodiments.

In several places throughout the present disclosure, guidance is provided through lists of examples, and these examples can be used in various combinations.

In each instance, the described list serves only as a representative group, and should not be interpreted as an exclusive list.

All of the publications, patents, and patent applications cited herein are incorporated herein by reference in their entirety.

Terms

The symbols and abbreviations in the present specification will be understood in the meaning usually used in the technical field of the present disclosure in the context of the present description, unless otherwise specified.

The term "comprising" in the present specification is used with the intention of including the meaning of the phrases "consisting essentially of" and "consisting of."

The steps, treatments, or operations described in the present specification can be performed at room temperature, unless otherwise specified.

The room temperature referred to in the present specification can mean a temperature in the range of 10 to 40° C.

The notation "$C_{n-m}$" (wherein n and m are each a number) used in the present specification means that the number of carbon atoms is n or more and m or less, as is usually understood by persons skilled in the art.

Unless otherwise specified, examples of the "halogen" as referred to in the present specification include a fluorine atom, a chlorine atom, a bromine atom, and an iodine atom.

The "organic group" as referred to in the present specification means a group formed by removing one hydrogen atom from an organic compound.

Examples of the "organic group" as referred to in the present specification include hydrocarbon groups optionally having one or more substituents, non-aromatic heterocyclic groups optionally having one or more substituents, heteroaryl groups optionally having one or more substituents, a cyano group, an aldehyde group, RO—, RS—, RCO—, $RSO_2$—, ROCO—, and $ROSO_2$— (wherein R is independently a hydrocarbon group optionally having one or more substituents, a non-aromatic heterocyclic group optionally having one or more substituents, or a heteroaryl group optionally having one or more substituents).

Examples of the "substituents" include halogen atoms, a cyano group, an amino group, alkoxy groups, and alkylthio groups. Two or more substituents may be identical to or different from each other.

Unless otherwise specified, examples of "hydrocarbon groups" as referred to in the present specification include alkyl, alkenyl, alkynyl, cycloalkyl, cycloalkenyl, cycloalkadienyl, aryl, and aralkyl.

Unless otherwise specified, examples of the "alkyl" as referred to in the present specification include linear or branched $C_{1-20}$ alkyl groups, such as methyl, ethyl, propyl (n-propyl, isopropyl), butyl (n-butyl, isobutyl, sec-butyl, tert-butyl), pentyl, and hexyl.

Unless otherwise specified, examples of the "alkoxy" as referred to in the present specification include linear or branched $C_{1-20}$ alkoxy groups, such as methoxy, ethoxy, propoxy (n-propoxy, isopropoxy), butoxy (n-butoxy, isobutoxy, sec-butoxy, tert-butoxy), pentyloxy, and hexyloxy.

Unless otherwise specified, examples of the "alkylthio" as referred to in the present specification include linear or branched $C_{1-20}$ alkylthio groups, such as methylthio, ethylthio, propylthio (n-propylthio, isopropylthio), butylthio (n-butylthio, isobutylthio, sec-butylthio, tert-butylthio), pentylthio, and hexylthio.

Unless otherwise specified, examples of the "alkenyl" as referred to in the present specification include linear or branched $C_{2-20}$ alkenyl groups, such as vinyl, 1-propen-1-yl, 2-propen-1-yl, isopropenyl, 2-buten-1-yl, 4-penten-1-yl, and 5-hexen-1-yl.

Unless otherwise specified, examples of the "alkynyl" as referred to in the present specification include linear or branched $C_{2-20}$ alkynyl groups, such as ethynyl, 1-propyn-1-yl, 2-propin-1-yl, 4-pentyn-1-yl, and 5-hexyn-1-yl.

Unless otherwise specified, examples of the "cycloalkyl" as referred to in the present specification include $C_{3-10}$ cycloalkyl groups, such as cyclopropyl, cyclobutyl, cyclopentyl, cyclohexyl, and cycloheptyl.

Unless otherwise specified, examples of the "cycloalkenyl" as referred to in the present specification include $C_{3-10}$ cycloalkenyl groups, such as cyclopropenyl, cyclobutenyl, cyclopentenyl, cyclohexenyl, and cycloheptenyl.

Unless otherwise specified, examples of the "cycloalkadienyl" as referred to in the present specification include $C_{4-10}$ cycloalkadienyl groups, such as cyclobutadienyl, cyclopentadienyl, cyclohexadienyl, cycloheptadienyl, cyclooctadienyl, cyclononadienyl, and cyclodecadienyl.

Unless otherwise specified, the "aryl" as referred to in the present specification can be monocyclic, bicyclic, tricyclic, or tetracyclic.

Unless otherwise specified, the "aryl" as referred to in the present specification can be a $C_{6-18}$ aryl group.

Unless otherwise specified, examples of the "aryl" as referred to in the present specification include phenyl, 1-naphthyl, 2-naphthyl, 2-biphenyl, 3-biphenyl, 4-biphenyl, and 2-anthryl.

Unless otherwise specified, examples of the "aralkyl" as referred to in the present specification include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylmethyl, 3-biphenylmethyl, and 4-biphenylmethyl.

Unless otherwise specified, the "non-aromatic heterocyclic group" as referred to in the present specification means a group formed by removing one hydrogen atom from a non-aromatic heterocycle.

Unless otherwise specified, the "non-aromatic heterocyclic group" as referred to in the present specification can be monocyclic, bicyclic, tricyclic, or tetracyclic.

Unless otherwise specified, the "non-aromatic heterocyclic group" as referred to in the present specification can be saturated or unsaturated.

Unless otherwise specified, the "non-aromatic heterocyclic group" as referred to in the present specification can be a 5- to 18-membered non-aromatic heterocyclic group.

Unless otherwise specified, the "non-aromatic heterocyclic group" as referred to in the present specification can be, for example, a non-aromatic heterocyclic group containing, in addition to carbon atoms, 1 to 4 heteroatoms selected from oxygen, sulfur, and nitrogen atoms as a ring-constituting atom.

Unless otherwise specified, examples of the "non-aromatic heterocyclic group" as referred to in the present specification include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like.

Unless otherwise specified, the "heteroaryl" as referred to in the present specification can be monocyclic, bicyclic, tricyclic, or tetracyclic.

Unless otherwise specified, the "heteroaryl" as referred to in the present specification can be, for example, a 5- to 18-membered heteroaryl group.

Unless otherwise specified, the "heteroaryl" as referred to in the present specification can be, for example, a heteroaryl group containing, in addition to carbon atoms, 1 to 4 heteroatoms selected from oxygen, sulfur, and nitrogen atoms as a ring-constituting atom.

Unless otherwise specified, examples of the "heteroaryl" as referred to in the present specification include "monocyclic heteroaryl groups" and "aromatic fused heterocyclic groups."

Unless otherwise specified, examples of the "monocyclic heteroaryl groups" as referred to in the present specification include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like.

Unless otherwise specified, examples of the "aromatic fused heterocyclic groups" as referred to in the present specification include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like.

Unless otherwise specified, examples of the "fluoroalkyl group optionally containing an oxygen atom between carbon atoms" as referred to in the present specification include linear or branched fluoro-$C_{1-10}$ alkyl groups, linear or branched fluoro-$C_{1-4}$ alkoxy-fluoro-$C_{1-4}$ alkyl groups, or linear or branched fluoro-$C_{1-4}$ alkoxy-fluoro-$C_{1-4}$ alkoxy-fluoro-$C_{1-4}$ alkyl groups such as $CF_3$—, $CH_3$—$CF_2$—, $CHF_2$—$CH_2$—, $CF_3$—$CH_2$—, $CF_3$—$CF_2$—, $CF_3$—$CF_2$—$CH_2$—, $CF_3$—$CF_2$—$CF_2$—, $(CF_3)_2CF$—, $CF_3$—O—$CF_2$—, $CF_3$—O—$CF(CF_3)$—, $CF_3$—$CF_2$—$CF_2$—$CF_2$—, $CF_3$—$CF_2$—$CF(CF_3)$—$CF_2$—, $CF_3$—O—$CH_2$—$CH_2$—, $CF_3O$—$CH(CF_3)$—$CH_2$—, $CF_3$—O—$CF_2$—$CF_2$—, $(CF_3CF_2)(CF_2)CF$—, $(CF_3)_3C$—, $CF_3$—$CF_2$—O—$CF_2$—, $CF_3$—$CF_2$—$CF_2$—$CF_2$—$CF_2$—, $CF_3$—$CF_2$—O—$CF_2$—$CF_2$—, $CF_3$—O—$CF_2$—O—$CF_2$—, $CF_3$—$CF_2$—$CF_2$—$CF_2$—$CF_2$—, $CF_3$—$CF_2$—$CF_2$—O—$CH_2$—$CF_2$—, $CF_3$—$CF_2$—$CF_2$—O—$CF_2$—$CF_2$—, $CF_3$—$CF_2$—$CF_2$—$CF_2$—$CF_2$—$CF_2$—, $CF_3$—$CF_2$—$CF_2$—$CF_2$—$CF_2$—, $CHF_2$—$CF_2$—$CF_2$—$CF_2$—$CF_2$—$CF_2$—$CF_2$—, $CF_3$—$CF_2$—$CH_2$—$CF_3$—$CF(CF_3)$—$CF_2$—, $CF_3$—$CF_2$—$CF(CF_3)$—, $CF_3$—$CF_2$—$CF_2$—O—$CF(CF_3)$—$CF_2$, $CF_3$—

CF$_2$—CF$_2$—O—CF(CF$_3$)—CF$_2$—O—CF(CF$_3$)—CF$_2$, and CF$_3$—CF$_2$—CF$_2$—O—[CF(CF$_3$)—CF$_2$—O—]$_2$—CF(CF$_3$)—CF$_2$—.

Unless otherwise specified, examples of the "fluoroalkoxy group optionally containing an oxygen atom between carbon atoms" include linear or branched fluoro-C$_{1-10}$ alkoxy groups or linear or branched fluoro-C$_{1-4}$ alkoxy-fluoro-C$_{1-4}$ alkoxy groups, such as CF$_3$—O—, CF$_3$—CH$_2$—O—, CF$_3$—CF$_2$—O—, CF$_3$—CF$_2$—CF$_2$—O—, CF$_3$—CF$_2$—CF$_2$—CF$_2$—O—, CF$_3$—O—CF$_2$—O—, CF$_3$—O—CF$_2$—CF$_2$—O—, CF$_3$—O—CH$_2$—CF$_2$—CF$_2$—O—, CF$_3$—CF$_2$—O—CF$_2$—CF$_2$—O—, CF$_3$—CF$_2$—CF$_2$—O—CH$_2$—CF$_2$—CF$_2$—O—, CF$_3$—CF$_2$—CF$_2$—O—CF$_2$—CF$_2$—CF$_2$—O—, CF$_3$—CF(CF$_3$)—O—, CF$_3$—CF$_2$—CF(CF$_3$)—O—, CF$_3$—CF(CF$_3$)—CF(CF$_3$)—O—, CF$_3$—CF$_2$—CF$_2$—O—CF(CF$_3$)—CF$_2$—O—, CF$_3$—CF$_2$—CF$_2$—O—[CF(CF$_3$)—CF$_2$—O—]$_2$—O—, and CF$_3$—CF$_2$—CF$_2$—O—[CF(CF$_3$)—CF$_2$—O—]$_3$—O—.

Method for Producing Compound Represented by Formula (1)

In one embodiment, the method for producing the compound represented by the following formula (1):

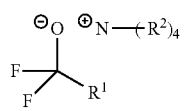

(1)

(wherein R$^1$ is a fluoroalkyl group optionally containing an oxygen atom between carbon atoms, or a fluoroalkoxy group optionally containing an oxygen atom between carbon atoms, and each R$^2$ is identical to or different from each other and is a hydrocarbon group) according to the present disclosure is a production method comprising the step of reacting a compound represented by the following formula (2):

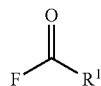

(2)

(wherein R$^1$ is as defined above) with a compound represented by the following formula (3):

(3)

(wherein R$^2$ is as defined above). According to this method, a metal-free and thermally stable fluoroalkoxide can be easily produced.

In formulas (1) and (2), R$^1$ is preferably a perfluoroalkyl group optionally containing an oxygen atom between carbon atoms, or a perfluoroalkoxy group optionally containing an oxygen atom between carbon atoms; and more preferably a perfluoro-C$_{1-8}$ alkyl group optionally containing an oxygen atom between carbon atoms, or a perfluoro-C$_{1-8}$ alkoxy group optionally containing an oxygen atom between carbon atoms.

In formulas (1) and (3), each R$^2$ is preferably alkyl, aryl, or aralkyl, more preferably alkyl, and even more preferably C$_{1-4}$ alkyl. From the viewpoint of reactivity and thermal stability, all R$^2$s are preferably methyl.

Preferable examples of the compound represented by formula (3) include the following compounds:

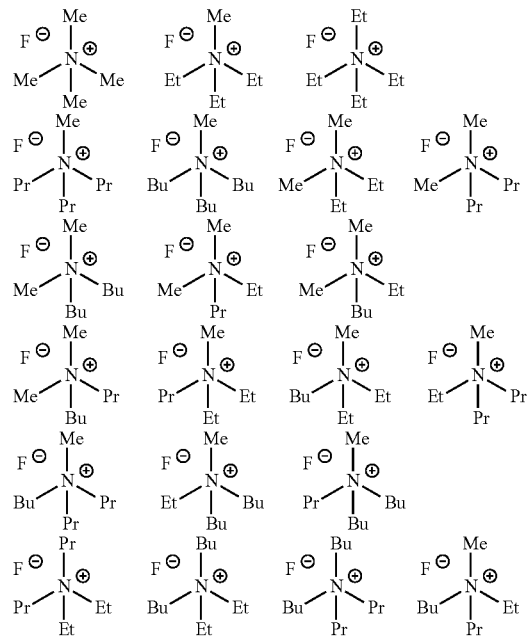

(wherein Me is methyl, Et is ethyl, Pr is propyl, and Bu is butyl).

The lower limit of the amount of the compound of formula (3) to be used can usually be 0.1 mol, preferably 0.2 mol, 0.3 mol, 0.4 mol, or 0.5 mol, per mol of the compound of formula (2).

The upper limit of the amount of the compound of formula (3) to be used can usually be 10 mol, preferably 5 mol, 4 mol, 3 mol, or 2 mol, per mol of the compound of formula (2).

The amount of the compound of formula (3) to be used is usually 0.1 to 10 mol, preferably 0.2 to 5 mol, more preferably 0.2 to 5 mol, and even more preferably 0.5 to 2 mol, per mol of the compound of formula (2).

The reaction between the compound represented by formula (2) and the compound represented by formula (3) is preferably performed in the presence of a solvent.

Examples of solvents include hydrocarbon solvents (e.g., chain hydrocarbons such as n-hexane; and aromatic hydrocarbons such as benzene, toluene, and p-xylene);

halogen solvents (e.g., haloalkanes such as dichloromethane and dichloroethane; and haloarenes such as chlorobenzene);

nitrile solvents (e.g., chain nitriles such as acetonitrile, propionitrile, and acrylonitrile; and cyclic nitriles such as benzonitrile);

amide solvents (e.g., carboxylic acid amides (e.g., chain amides such as formamide, N-methylformamide, and N,N-diethylformamide; and cyclic amides such as N-methylpyrrolidone); and amide phosphate (e.g., hexamethylphosphoric amide)); and ether solvents (e.g., chain ethers such as diethyl ether; and cyclic ethers such as tetrahydrofuran, and dioxane);

urea solvents (e.g., N,N-dimethylpropylene urea);

ester solvents (e.g., esters of acetic acid);

sulfoxide solvents (e.g., dimethyl sulfoxide);

nitro solvents (e.g., nitromethane and nitrobenzene);

ketone solvents (e.g., acetone and methyl ethyl ketone); a mixed solvent of two or more of these; and the like.

The solvent is preferably a halogen solvent, a urea solvent, an amide solvent, a sulfoxide solvent, an ester solvent, a nitrile solvent, an ether solvent, or a mixed solvent of two or more of these; more preferably a halogen solvent, a nitrile solvent, an amide solvent, an ether solvent, or a mixed solvent of two or more of these; and even more preferably a nitrile solvent.

In the reaction between the compound represented by formula (2) and the compound represented by formula (3), the reaction temperature and the reaction time are not particularly limited as long as the reaction proceeds. The reaction can be accelerated by heating.

The lower limit of the reaction temperature can be, for example, −20° C., preferably −10° C., −5° C., 0° C., 5° C., 10° C., or 15° C.

The upper limit of the reaction temperature can be, for example, 110° C., preferably 100° C., 90° C., 80° C., 70° C., 60° C., 50° C., or 40° C.

The reaction temperature is, for example, in the range of −20 to 110° C., preferably 0 to 70° C., and more preferably 15 to 40° C.

The reaction time is, for example, in the range of 0.5 to 48 hours, preferably 1 to 24 hours.

Composition

The composition according to one embodiment of the present disclosure is a composition containing a compound represented by formula (1) and a compound represented by the following formula (4):

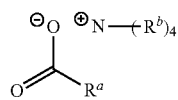

(wherein $R^a$ is a fluoroalkyl group optionally containing an oxygen atom between carbon atoms, or a fluoroalkoxy group optionally containing an oxygen atom between carbon atoms, and each $R^b$ is identical to or different from each other).

The compound represented by formula (1) can be selected from the compounds exemplified in the above section "Method for Producing Compound Represented by Formula (1)."

In formula (4), $R^a$ is preferably a perfluoroalkyl group optionally containing an oxygen atom between carbon atoms, or a perfluoroalkoxy group optionally containing an oxygen atom between carbon atoms; more preferably a perfluoro-$C_{1-8}$ alkyl group optionally containing an oxygen atom between carbon atoms, or a perfluoro-$C_{1-8}$ alkoxy group optionally containing an oxygen atom between carbon atoms.

In formula (4), each $R^b$ is preferably alkyl, aryl, or aralkyl; more preferably alkyl; and even more preferably $C_{1-4}$ alkyl. It is also preferable that all $R^b$s are methyl.

A suitable example of the compound represented by formula (4) is a compound wherein the anion represented by —OC(=O)$R^a$ is (perfluoro-$C_{1-8}$ alkyl) carbonyloxy, and the cation represented by +N($R^b$)$_4$ is a compound selected from the following compounds:

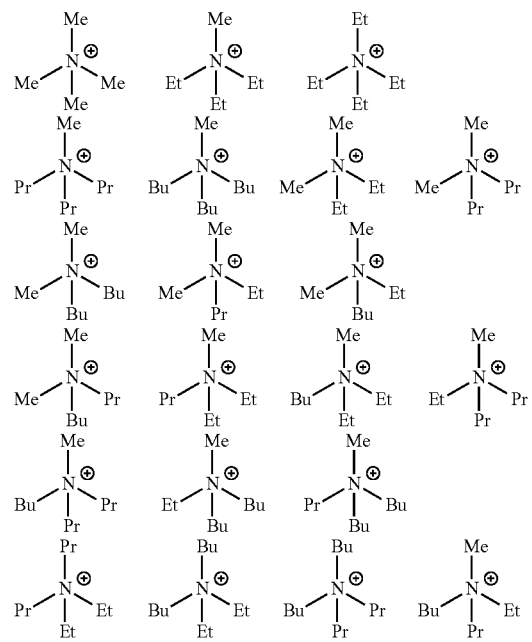

(wherein Me is methyl, Et is ethyl, Pr is propyl, and Bu is butyl).

The compound represented by formula (4) can be, for example, a hydrolyzate of the compound represented by formula (1). In this case, $R^1$ in formula (1) and $R^a$ in the formula (4) are identical to each other, and $R^2$ in formula (1) and $R^b$ in formula (4) are identical to each other.

The lower limit of the content (molar ratio) of the compound represented by formula (1) can be, for example, 70%, preferably 80%, and more preferably 85%, when the sum of the content of the compound represented by formula (1) and the content of the compound represented by formula (4) is defined as 100%.

The upper limit of the content (molar ratio) of the compound represented by formula (1) can be, for example, 99%, 98%, 97%, 96%, or 95%, when the sum of the content of the compound represented by formula (1) and the content of the compound represented by formula (4) is defined as 100%.

The content of the compound represented by formula (1) (molar ratio) can be, for example, in the range of 70 to 99%, 80 to 99%, or 85 to 99%, when the sum of the content of the compound represented by formula (1) and the content of the compound represented by formula (4) is defined as 100%.

The content of the compound represented by formula (1) is a value calculated from the intensity ratio of a peak of δ −20 to −40 ppm (a peak derived from the compound represented by formula (1)) and a peak of δ −112 to −118 ppm (derived from the compound represented by formula (4)) in the $^{19}$F-NMR spectrum.

Fluoroalkoxylating Agent

The fluoroalkoxylating agent according to one embodiment of the present disclosure comprises a composition containing a compound represented by formula (1) and a compound represented by formula (4). The composition contained in the fluoroalkoxylating agent can be selected from those exemplified in the above section "Composition."

The fluoroalkoxylating agent is preferably a perfluoroalkoxylating agent.

Method for Producing Compound Represented by Formula (5)

In one embodiment, the method for producing the compound represented by the following formula (5):

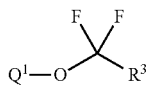
(5)

(wherein $R^3$ is a fluoroalkyl group optionally containing an oxygen atom between carbon atoms, or a fluoroalkoxy group optionally containing an oxygen atom between carbon atoms, and $Q^1$ is an organic group) is a production method comprising the step of reacting a compound represented by the following formula (6):

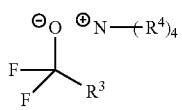
(6)

(wherein $R^3$ is as defined above, and each $R^4$ is identical to or different from each other and is a hydrocarbon group) with a compound represented by the following formula (7):

$$Q^1\text{-L} \qquad (7)$$

(wherein $Q^1$ is as defined above, and L is a leaving group).

In formulas (5) and (6), $R^3$ is preferably a perfluoroalkyl group optionally containing an oxygen atom between carbon atoms, or a perfluoroalkoxy group optionally containing an oxygen atom between carbon atoms, more preferably a perfluoro-$C_{1-8}$ alkyl group optionally containing an oxygen atom between carbon atoms, or a perfluoro-$C_{1-8}$ alkoxy group optionally containing an oxygen atom between carbon atoms.

In formula (6), each $R^4$ is preferably alkyl, aryl, or aralkyl; more preferably alkyl; and even more preferably $C_{1-4}$ alkyl. In view of reactivity and thermal stability, it is also preferable that all $R^4$s are methyl.

A suitable example of the compound represented by formula (6) is that the anion represented by —$OCF_2R^3$ is perfluoro-$C_{1-9}$ alkoxide and the cation represented by $+N(R^4)_4$ is a compound selected from the following compounds:

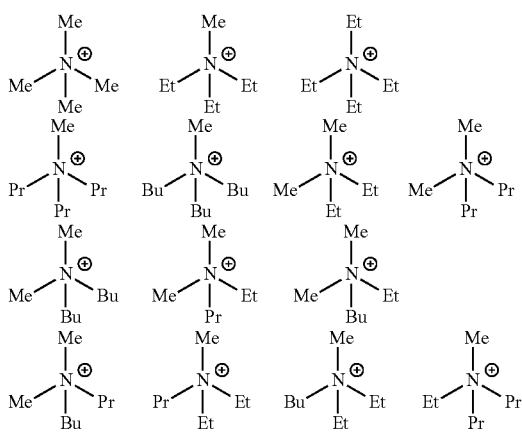
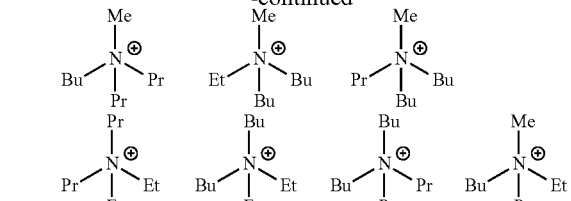

(wherein Me is methyl, Et is ethyl, Pr is propyl, and Bu is butyl).

In formula (7), $Q^1$ is preferably a hydrocarbon group optionally having one or more substituents; more preferably a hydrocarbon group, and even more preferably alkyl, alkenyl, aryl, or aralkyl.

Examples of leaving groups represented by L include halogen atoms (e.g., chlorine, bromine, iodine), alkylsulfonyloxy groups (e.g., mesyloxy), haloalkylsulfonyloxy groups (e.g., trifluoromethyloxy), and arylsulfonyloxy groups (e.g., tosyloxy). L is preferably a halogen atom, and is more preferably one species selected from chlorine, bromine, and iodine.

Preferable examples of the compound represented by formula (7) include alkyl halides (e.g., $C_{2-20}$ alkyl bromides such as ethyl bromide, propyl bromide, and butyl bromide; and $C_{2-20}$ alkyl chlorides wherein bromine of such bromides is replaced with chlorine), alkenyl halides (e.g., $C_{3-20}$ alkenyl bromides, such as allyl bromide, 3-butenyl bromide, 4-pentenyl bromide, and 5-hexenyl bromide; and $C_{3-20}$ alkenyl chlorides wherein bromine of such bromides is replaced with chlorine), aryl halides (e.g., $C_{6-10}$ aryl bromides such as bromobenzene; and $C_{6-10}$ aryl chlorides wherein bromine of such bromides is replaced with chlorine), and aralkyl halides (e.g., $C_{6-10}$ aryl-$C_{1-10}$ alkyl bromides such as benzyl bromide and phenethyl bromide; and $C_{6-10}$-aryl-$C_{1-10}$ alkyl chlorides wherein bromine of such bromides is replaced with chlorine).

The lower limit of the amount of the compound of formula (6) to be used can usually be 0.5 mol, preferably 0.6 mol, 0.7 mol, 0.8 mol, or 0.9 mol, per mol of the compound of formula (7).

The upper limit of the amount of the compound of formula (6) to be used can usually be 10 mol, preferably 9 mol, 8 mol, 7 mol, 6 mol, or 5 mol, per mol of the compound of formula (7).

The amount of the compound of formula (6) to be used can usually be in the range of 0.5 to 10 mol, and preferably 0.9 to 5 mol, per mol of the compound of formula (7).

The reaction between the compound represented by formula (6) and the compound represented by formula (7) is preferably performed in the presence of an auxiliary agent.

Examples of the auxiliary agent include silver tetrafluoroborate, silver hexafluorophosphate, and the like. These auxiliary agents can be used alone, or in a combination of two or more.

The amount of the auxiliary agent to be used is usually in the range of 0.1 to 10 mol, and preferably 0.2 to 5 mol, per mol of the compound represented by formula (7).

The reaction between the compound represented by formula (6) and the compound represented by formula (7) is preferably performed in the presence of a solvent.

Examples of solvents include hydrocarbon solvents (e.g., chain hydrocarbons such as n-hexane; and aromatic hydrocarbons such as benzene, toluene, and p-xylene);

halogen solvents (e.g., haloalkanes such as dichloromethane and dichloroethane; and haloarenes such as chlorobenzene);
nitrile solvents (e.g., chain nitriles such as acetonitrile, propionitrile, and acrylonitrile; and cyclic nitriles such as benzonitrile);
amide solvents (e.g., carboxylic acid amides (e.g., chain amides such as formamide, N-methylformamide, and N,N-diethylformamide; and cyclic amides such as N-methylpyrrolidone), and phosphoric acid amides (e.g., hexamethylphosphoric acid amide));
ether solvents (e.g., chain ethers such as diethyl ether; and cyclic ethers such as tetrahydrofuran, and dioxane);
urea solvents (e.g., N,N-dimethylpropylene urea);
ester solvents (e.g., esters of acetic acid);
sulfoxide solvents (e.g., dimethyl sulfoxide);
nitro solvents (e.g., nitromethane and nitrobenzene);
ketone solvents (e.g., acetone and methyl ethyl ketone);
a mixed solvent of two or more of these;
and the like.

The solvent is preferably a halogen solvent, a urea solvent, an amide solvent, a sulfoxide solvent, an ester solvent, a nitrile solvent, an ether solvent, or a mixed solvent of two or more of these, and more preferably a halogen solvent, a nitrile solvent, an amide solvent, an ether solvent, or a mixed solvent of two or more of these, and even more preferably a nitrile solvent.

In the reaction between the compound represented by formula (6) and the compound represented by formula (7), the reaction temperature and the reaction time are not particularly limited as long as the reaction proceeds. The reaction can proceed by heating.

The lower limit of the reaction temperature can be, for example, 0° C., and preferably 5° C., 10° C., or 15° C.

The upper limit of the reaction temperature can be, for example, 100° C., and preferably 95° C., 90° C., 85° C., or 80° C.

The reaction temperature is, for example, in the range of 0 to 100° C., and preferably 15 to 80° C.

The reaction time is, for example, in the range of 0.5 to 24 hours, preferably 1 to 24 hours, and more preferably 1 to 18 hours.

The reaction product obtained from the compound represented by formula (6) and the compound represented by formula (7) may include, for example, a compound represented by the following formula (5'):

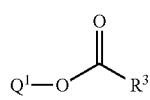

(5')

(wherein $R^3$ and $Q^1$ are as defined above) as a by-product.

In the reaction product, the content (molar ratio) of the compound represented by formula (5') is, for example, 30% or less, preferably 20% or less, and more preferably 15% or less, when the total of the content of the compound represented by formula (5) and the content of the compound represented by formula (5') is defined as 100%. The content of the compound represented by formula (5') can be calculated from the $^{19}$F-NMR spectrum peak intensity. The reaction product can be purified by a conventional method, such as filtration or column chromatography.

The present disclosure includes the following embodiments.

Item 1. A method for producing a compound represented by the following formula (1):

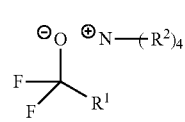

(1)

(wherein $R^1$ is a fluoroalkyl group optionally containing an oxygen atom between carbon atoms, or a fluoroalkoxy group optionally containing an oxygen atom between carbon atoms, and
each $R^2$ is identical to or different from each other and is a hydrocarbon group),
the method comprising the step of reacting
a compound represented by the following formula (2):

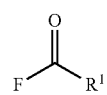

(2)

(wherein $R^1$ is as defined above)
with a compound represented by the following formula (3):

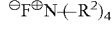

(3)

(wherein $R^2$ is as defined above).

Item 2. The method according to Item 1, wherein each $R^2$ is identical to or different from each other and is alkyl.

Item 3. The method according to Item 1 or 2, wherein each $R^2$ is identical to or different from each other and is $C_{1-4}$ alkyl.

Item 4. The method according to any one of Items 1 to 3, wherein all $R^2$s are methyl.

Item 5. The method according to any one of Items 1 to 4, wherein $R^1$ is a perfluoro-$C_{1-8}$ alkyl group optionally containing an oxygen atom between carbon atoms, or a perfluoro-$C_{1-8}$ alkoxy group optionally containing an oxygen atom between carbon atoms.

Item 6. The method according to any one of Items 1 to 5, wherein the reaction is performed in the presence of at least one solvent selected from the group consisting of halogen solvents, urea solvents, amide solvents, sulfoxide solvents, ester solvents, nitrile solvents, and ether solvents.

Item 7. The method according to any one of Items 1 to 6, wherein the reaction is performed in the presence of at least one solvent selected from the group consisting of halogen solvents, amide solvents, nitrile solvents, and ether solvents.

Item 8. The method according to any one of Items 1 to 7, wherein the reaction is performed in the presence of a nitrile solvent.

Item 9. A composition comprising
a compound represented by formula (1):

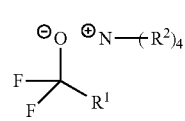

(1)

(wherein $R^1$ is a fluoroalkyl group optionally containing an oxygen atom between carbon atoms, or a fluoroalkoxy group optionally containing an oxygen atom between carbon atoms, and each $R^2$ is identical to or different from each other and is a hydrocarbon group), and a compound represented by formula (4):

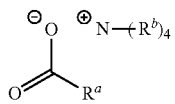

(4)

(wherein $R^a$ is a fluoroalkyl group optionally containing an oxygen atom between carbon atoms, or a fluoroalkoxy group optionally containing an oxygen atom between carbon atoms, and each $R^b$ is identical to or different from each other and is a hydrocarbon group), wherein when the sum of the content of the compound represented by formula (1) and the content of the compound represented by formula (4) is defined as 100%, the content of the compound represented by formula (1) is 70% or more in terms of molar ratio.

Item 10. The composition according to Item 9, wherein each $R^2$ is identical to or different from each other and is alkyl, and each $R^b$ is identical to or different from each other and is alkyl.

Item 11. The composition according to Item 9 or 10, wherein each $R^2$ is identical to or different from each other and is $C_{1-4}$ alkyl, and each $R^b$ is identical to or different from each other and is $C_{1-4}$ alkyl.

Item 12. The composition according to any one of Items 9 to 11 wherein all $R^2$s are methyl, and all $R^b$s are methyl.

Item 13. The composition according to any one of Items 9 to 12, wherein $R^1$ is a perfluoro-$C_{1-8}$ alkyl group optionally containing an oxygen atom between carbon atoms, or a perfluoro-$C_{1-8}$ alkoxy group optionally containing an oxygen atom between carbon atoms, and $R^a$ is a perfluoro-$C_{1-8}$ alkyl group optionally containing an oxygen atom between carbon atoms, or a perfluoro-$C_{1-8}$ alkoxy group optionally containing an oxygen atom between carbon atoms.

Item 14. A fluoroalkoxylating agent comprising the composition of any one of Items 9 to 13.

Item 15. A method for producing a compound represented by the following formula (5):

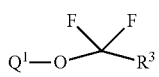

(5)

(wherein $R^3$ is a fluoroalkyl group optionally containing an oxygen atom between carbon atoms, or a fluoroalkoxy group optionally containing an oxygen atom between carbon atoms, and $Q^1$ is an organic group),
the method comprising the step of reacting
a compound represented by the following formula (6):

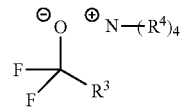

(6)

(wherein $R^3$ is as defined above, and each $R^4$ is identical to or different from each other and is a hydrocarbon group)
with a compound represented by the following formula (7):

$Q^1$-L (7)

(wherein $Q^1$ is as defined above and L is a leaving group).

Item 16. The method according to Item 15, wherein $Q^1$ is a hydrocarbon group optionally having one or more substituents.

Item 17. The method according to Item 15 or 16, wherein L is a halogen atom.

Item 18. The method according to any one of Items 15 to 17, wherein each $R^4$ is identical to or different from each other and is alkyl.

Item 19. The method according to any one of Items 15 to 18, wherein each $R^4$ is identical to or different from each other and is $C_{1-4}$ alkyl.

Item 20. The method according to any one of Items 15 to 19, wherein all $R^4$s are methyl.

Item 21. The method according to any one of Items 15 to 20, wherein $R^3$ is a perfluoro-$C_{1-8}$ alkyl group optionally containing an oxygen atom between carbon atoms, or a perfluoro-$C_{1-8}$ alkoxy group optionally containing an oxygen atom between carbon atoms.

Item 22. The method according to any one of Items 15 to 21, wherein the reaction is performed at a temperature in the range of 0 to 100° C. for a period of 1 to 24 hours.

EXAMPLES

One embodiment according to the present disclosure is described below in more detail with reference to Examples. However, the present disclosure is not limited thereto or thereby.

Example 1: Synthesis of Tetramethylammonium Perfluorooctan-1-olate

In a nitrogen atmosphere, 23.8 mg of tetramethylammonium fluoride was weighed in a 10 mL pressure-resistant container, and 1 mL of acetonitrile was added.

104 mg of perfluorooctanoyl fluoride and 0.2 mL of acetonitrile were added to the container.

After stirring at room temperature for 30 minutes, the contents of the container were analyzed by $^{19}$F NMR. The analysis results indicated that the title alkoxide was obtained as a mixture with tetramethylammonium perfluoroheptanoate in a molar ratio of 87:13.

$^{19}$F NMR (376 MHz, CD$_3$CN): δ−34.3 (br-s, 2F), −80.4 (t, J=9.7 Hz, 3F), −120.4 (t, J=13.5 Hz, 2F), −120.8 to −121.5 (m, 6F), −122.0 (m, 2F), −125.4 (n, 2F) ppm.

Example 2: Synthesis of Tetramethylammonium Perfluorohexan-1-olate

In a nitrogen atmosphere, 23.8 mg of tetramethylammonium fluoride was weighed in a 10 mL pressure-resistant container, and 1 mL of acetonitrile was added.

79 mg of perfluorohexanoyl fluoride and 0.2 mL of acetonitrile were added to the container.

After stirring at room temperature for 30 minutes, the contents of the container were analyzed by $^{19}$F NMR. The analysis results indicated that the title alkoxide was obtained as a mixture with tetramethylammonium perfluorohexanoate in a molar ratio of 88:12.

$^{19}$F NMR (376 MHz, CD$_3$CN): δ −25.5 (t, J=8.8 Hz, 2F), −80.8 (t, J=10.5 Hz, 2F), −120.6 to −120.7 (M, 2F), −121.6 (br-s, 2F), −122.3 to −122.4 (m, 2F), −125.7 (t, J=13.5 Hz, 2F) ppm.

Example 3: Synthesis of Tetramethylammonium Perfluoro-2-propoxypropan-1-olate In a nitrogen atmosphere, 23.8 mg of tetramethylammonium fluoride was weighed in a 10 mL pressure-resistant container, and 1 mL of acetonitrile was added.

83 mg of 2-(heptafluoropropoxy)tetrafluoropropionyl fluoride and 0.2 mL of acetonitrile were added to the container.

After stirring at room temperature for 30 minutes, the content of the container was analyzed by $^{19}$F NMR. The analysis results indicated that the title alkoxide was produced as a mixture with tetramethylammonium perfluoro-2-propoxypropanoate in a molar ratio of 84:16.

$^{19}$F NMR (376 MHz, CD$_3$CN): δ −29.8 (br-s, 2F), −79.7 (d, J=9.0 Hz, 3F), −81.1 (t, J=9.0 Hz, 3F), −81.7 (s, 2F), −129.5 (t, J=9.0 Hz, 2F), −137.7 (t, J=20.3 Hz, 1F) ppm.

Example 4: Synthesis of Benzyl Perfluorooctyl Ether

In a nitrogen atmosphere, 70 mg of tetramethylammonium fluoride was weighed in a 10 mL container, and 4 mL of acetonitrile was added. 325 mg of perfluoroheptaacyl fluoride and 0.8 mL of acetonitrile were added to the container.

After stirring at room temperature for 30 minutes, 35.7 µL of benzyl bromide, 70.1 mg of silver tetrafluoroborate, and 0.4 mL of acetonitrile were added.

The container was heated at 45° C. for 8 hours.

After the container was cooled to room temperature, the contents of the container were filtered through Celite using dichloromethane, and purified by silica gel column chromatography. The desired title ether was obtained with a molar yield of 52% relative to benzyl bromide.

$^{19}$F NMR: (376 MHz, CDCl$_3$): δ−80.8 (t, J=9.0 Hz, 3F), −8.47 (br-s, 2F), −121.9 (br-s, 6F), −122.7 (br-s, 2F), −125.1 (br-s, 2F), −126.2 (br-s, 2F) ppm.

Example 5: Synthesis of Allyl Perfluorooctyl Ether

In a nitrogen atmosphere, 72.6 mg of tetramethylammonium fluoride was weighed in a 10 mL container, and 2 mL of acetonitrile was added.

325 mg of perfluoroheptaacyl fluoride and 0.8 mL of acetonitrile were added.

After stirring at room temperature for 30 minutes, 25.3 µL of allyl bromide, 70.1 mg of silver tetrafluoroborate, and 0.4 mL of acetonitrile were added.

The container was heated at 45° C. for 8 hours.

After the container was cooled to room temperature, the contents of the container were filtered through Celite using dichloromethane, and then analyzed by $^{19}$F NMR. The analysis results indicated that the desired title ether was obtained with a molar yield of 38% relative to allyl bromide.

$^{19}$F NMR (376 MHz, CDCl$_3$): δ −80.6 (t, J=8.1 Hz, 3F), −84.7 (br-s, 12F), −122.0 (br-s, 2F), −122.6 (br-s, 2F), −125.0 (br-s, 2F), −126.0 (br-s, 2F) ppm.

Example 6: Synthesis of 2-(Perfluorooctyloxy)ethyl Acetate

In a nitrogen atmosphere, 70 mg of tetramethylammonium fluoride was weighed in a 10 mL container, and 4 mL of acetonitrile was added.

325 mg of perfluoroheptaacyl fluoride and 0.8 mL of acetonitrile were added to the container.

After stirring at room temperature for 30 minutes, 33.2 µL of ethyl bromoacetate, 70.1 mg of silver tetrafluoroborate, and 0.4 mL of acetonitrile were added.

The container was heated at 45° C. for 9 hours.

After the container was cooled to room temperature, the contents of the container were filtered through Celite using dichloromethane, and then analyzed by $^{19}$F NMR. The analysis results indicated that the desired title ether was obtained with a molar yield of 22% with respect to ethyl bromoacetate.

$^{19}$F NMR (376 MHz, CDCl$_3$): δ−81.5 (t, J=9.0 Hz, 3F), −85.5 (br-s, 2F), −122.3 to −122.4 (m, 6F), −123.2 (br-s, 2F), −125.6 (br-s, 2F), −126.6 (br-s, 2F) ppm.

The invention claimed is:
1. A composition comprising
a compound represented by formula (1):

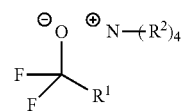

(1)

wherein R$^1$ is a fluoroalkyl group optionally containing an oxygen atom between carbon atoms, or a fluoroalkoxy group optionally containing an oxygen atom between carbon atoms, and each R$^2$ is identical to or different from each other and is a hydrocarbon group, and a compound represented by formula (4):

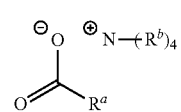

(4)

wherein R$^a$ is a fluoroalkyl group optionally containing an oxygen atom between carbon atoms, or a fluoroalkoxy group optionally containing an oxygen atom between carbon atoms, and each R$^b$ is identical to or different from each other and is a hydrocarbon group, wherein $R^1$ is not $CF_3$, $C_2F_5$, or $C_3F_7$, and $R^a$ is not $CF_3$, $C_2F_5$, or $C_3F_7$, and wherein when the sum of the content of the compound represented by formula (1) and the content of the compound represented by formula (4) is defined as 100%, the content of the compound represented by formula (1) is 70-95% in terms of molar ratio.

2. The composition according to claim 1, wherein each $R^2$ is identical to or different from each other and is alkyl, and each $R^b$ is identical to or different from each other and is alkyl.

3. The composition according to claim 1, wherein each $R^2$ is identical to or different from each other and is $C_1$-4 alkyl, and each $R^b$ is identical to or different from each other and is $C_1$-4 alkyl.

4. The composition according to claim 1 wherein all $R^2$s are methyl, and all $R^b$s are methyl.

5. The composition according to claim 1, wherein $R^1$ is a perfluoro-$C_{4-8}$ alkyl group optionally containing an oxygen atom between carbon atoms, or a perfluoro-$C_{1-8}$ alkoxy group optionally containing an oxygen atom between carbon atoms, and $R^a$ is a perfluoro-$C_{4-8}$ alkyl group optionally containing an oxygen atom between carbon atoms, or a perfluoro-$C_{1-8}$ alkoxy group optionally containing an oxygen atom between carbon atoms.

6. A fluoroalkoxylating agent comprising the composition of claim 1.

* * * * *